(12) United States Patent
Cao et al.

(10) Patent No.: US 6,699,875 B2
(45) Date of Patent: Mar. 2, 2004

(54) CASCADE ESTERS OF CAMPTOTHECINS AND METHODS OF TREATING CANCER USING THESE COMPOUNDS

(75) Inventors: Zhisong Cao, Friendswood, TX (US); Beppino C. Giovanella, Houston, TX (US)

(73) Assignee: The Stehlin Foundation for Cancer Research, Houston, TX (US)

( * ) Notice: Subject to any disclaimer, the term of this patent is extended or adjusted under 35 U.S.C. 154(b) by 3 days.

(21) Appl. No.: 10/139,778

(22) Filed: May 6, 2002

(65) Prior Publication Data

US 2003/0216421 A1 Nov. 20, 2003

(51) Int. Cl.[7] .................. A61K 31/435; C07D 491/052; C07D 31/47
(52) U.S. Cl. .......................................... 514/283; 546/48
(58) Field of Search ............................ 546/48; 514/283

(56) References Cited

U.S. PATENT DOCUMENTS

| | | | |
|---|---|---|---|
| 4,399,282 A | 8/1983 | Miyasaka et al. | 546/48 |
| RE32,518 E | 10/1987 | Miyasaka et al. | 546/48 |
| 5,552,154 A | 9/1996 | Giovanella et al. | 424/449 |
| 5,652,244 A | 7/1997 | Giovanella et al. | 514/283 |
| 5,731,316 A | 3/1998 | Cao et al. | 514/283 |
| 5,880,131 A | 3/1999 | Greenwald et al. | 514/279 |
| 5,889,017 A | 3/1999 | Giovanella et al. | 514/283 |
| 5,922,877 A | 7/1999 | Cao | 546/48 |
| 5,965,566 A | 10/1999 | Greenwald et al. | 514/279 |
| 5,968,943 A | 10/1999 | Cao et al. | 514/283 |
| 6,040,313 A | 3/2000 | Wall et al. | 514/283 |
| 6,080,751 A | 6/2000 | Stehlin et al. | 514/283 |
| 6,096,336 A | 8/2000 | Cao et al. | 424/450 |
| 6,120,793 A | 9/2000 | Cao et al. | 424/449 |
| 6,166,029 A | 12/2000 | Giovanella et al. | 514/283 |
| 6,218,399 B1 | 4/2001 | Cao et al. | 514/283 |
| 6,228,855 B1 | 5/2001 | Cao et al. | 514/224.2 |
| 6,342,506 B1 | 1/2002 | Giovanella et al. | 514/283 |
| 6,350,756 B1 | 2/2002 | Yang et al. | 514/283 |
| 6,407,118 B1 | 6/2002 | Cao et al. | 514/283 |
| 6,407,239 B1 | 6/2002 | Cao et al. | 546/48 |
| 2001/0031761 A1 | 10/2001 | Cao et al. | 514/283 |
| 2002/0049324 A1 | 4/2002 | Cao et al. | 546/48 |

FOREIGN PATENT DOCUMENTS

WO   WO 03/014069   2/2003

OTHER PUBLICATIONS

Article, "Plant Antitumor Agents," by Wall et al., Journal of Medicinal Chemistry, 1993, vol. 36, No. 18, pp. 2689–2700.
Article, "Camptothecin–20–PEG Ester Transport Forms: the Effect of Spacer Groups on Antitumor Activity," by Greenwald et al., Bioorganic & Medicinal Chemistry 6, 1998, p. 551–562.
International Search Report, dated Aug. 29, 2003, for PCT/US03/12399.

*Primary Examiner*—Bernard Dentz
(74) *Attorney, Agent, or Firm*—Kilyk & Bowersox, P.L.L.C.

(57) ABSTRACT

Cascade esters of camptothecin are described. Processes for making these compounds and for using them in cancer treatment are also described.

34 Claims, No Drawings

CASCADE ESTERS OF CAMPTOTHECINS AND METHODS OF TREATING CANCER USING THESE COMPOUNDS

FIELD OF THE INVENTION

The present invention is directed to cascade esters of camptothecin and is also directed to compositions including derivatives of cascade esters of camptothecin in delivery systems, preferably derivatives having low toxicity and side effects. The present invention also relates to the use of these derivatives for cancer or tumor treatment in mammals. The disclosures of all documents referred to in this application are incorporated herein in their entirety by reference.

BACKGROUND OF THE INVENTION

Camptothecin, a cytotoxic alkaloid first isolated from the wood and bark of Camptotheca Acuminata (Nyssaceae) by Wall and his coworkers (*J. Am. Chem. Soc.* 88, 3888, 1966), was shown to have antitumor activity against the mouse leukemia L 1210 system. The structure of camptothecin, an alkaloid which has a commonly occurring indole alkaloid group (Heckendorf et al, *J Org. Chem.* 41, 2045, 1976), is shown below as Formula (X).

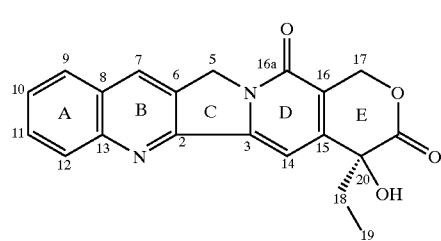

(X)

This compound ("CPT") has a pentacyclic ring system with only one asymmetrical center in ring E with a 20(S)-configuration. The pentacyclic ring system includes a pyrrolo [3, 4-b] quinoline moiety (rings A, B and C), a conjugated pyridone (ring D), and a six-membered lactone (ring E) with an a α-hydroxyl group. Camptothecin was of great interest from the time of its initial isolation due to its noteworthy activity in the mouse leukemia L 1210 system. Earlier data for the antitumor activity of camptothecin were obtained by employing experimentally transplanted malignancies such as leukemia L 1210 in mice, or Walker 256 tumor in rats (*Chem. Rev.* 23, 385, 1973, *Cancer Treat. Rep.* 60, 1007, 1967). Subsequent clinical studies showed that this compound was not usable as an anticancer agent in vivo due to its high toxicity. Camptothecin itself is insoluble in water. Therefore, camptothecin was evaluated clinically as a water-soluble sodium carboxylate salt in the early times. This form of camptothecin produced severe toxicity and seemed devoid of anticancer activity (Gottlieb et al, *Cancer Chemother. Rep.* 54, 461, 1970, and 56, 103, 1972, Muggia et al, *Cancer Chemother. Rep.* 56, 515, 1972, Moertel et al, *Cancer Chemother. Rep.* 56, 95, 1972, and Schaeppi et al, *Cancer Chemother. Rep.* 5:25, 1974). These results caused the discontinuation of phase II trials. Continued evaluation of this agent showed that the sodium carboxylate salt is only 10% as potent as the native camptothecin with the closed lactone ring intact (Wall et al, *In International Symposium on Biochemistry And Physiology of The Alkaloids, Mothes et al, eds, Academie—Verlag,* Berlin, 77, 1969, Giovanella et al, *Cancer res.* 51, 3052, 1991). In addition, important parameters for antitumor activity in the camptothecin family have been established (Wall et al, *Ann. Rev., Pharmacol. Toxicol.* 17, 117, 1977). These results indicate that an intact lactone ring E and α-hydroxyl group are essential for antitumor activity.

In 1989, Giovanella et al. found that some of the non-water soluble derivatives of camptothecin have high antitumor activity against xenograft of human tumors (Giovanella et al., *Science*, 246, 1046, 1989). It has also been shown that administration of camptothecin with closed lactone ring is superior to injections of water-soluble carboxylate salt (Giovanella et al, *Cancer Res.*, 51, 3052, 1991). These findings further confirmed the importance of the intact lactone ring to biological activity.

Ring opening of 20(S)-camptothecin ("CPT") leads to much more potent anticancer activity in mice than in humans. In effect, CPT administered intramuscularly ("i.m."), subcutaneously ("s.c."), and intrastomach ("i.s.") has proved to be a very potent anticancer agent against human tumors in mice, i.e., when growing as xenotransplants in nude mice (Giovanella et al, Cancer Res. 51:3052, 1991). However, when tumors were treated with CPT in humans, a lower degree of anticancer activity in humans, than in mice, was exhibited (Stehlin et al., In Camptothecins: New Anticancer Agents, 1995, CRC Press, pp. 59–65).

The same phenomenon was observed with other CPT-derivatives. In mice, 9-nitrocamptothecin ("9NC") has proven to be 2–3 times more potent than CPT against human tumor xenografts causing the total eradication of all the human malignancies treated (Pantazis et al., Cancer Res. 53:1577, 1993; Pantazis et al., Int. J. Cancer 53:863, 1995).

Pharmacological studies demonstrated that the majority (57%) of the 9NC drug present in the plasma after i.s. administration is in the closed lactone form. Pharmacological studies on the plasma levels of 9NC after oral administration to Phase I clinical trial patients demonstrate that, on average, only ~3% of the drug present is in the closed lactone form.

In perfect agreement with such findings, the clinical responses in this group of patients, although higher than those obtained with CPT are still a far cry below the results obtained in mice (32/32 complete tumor regressions in mice versus 2/32 in humans). Clearly, there is a pressing need for a modification which will slow and delay the lactone ring opening upon its entrance into the blood circulation.

Ring opening is particularly problematic in that camptothecins exist in two distinct forms at physiological pH, i.e., 7 or above, as shown in the following equilibrium equation:

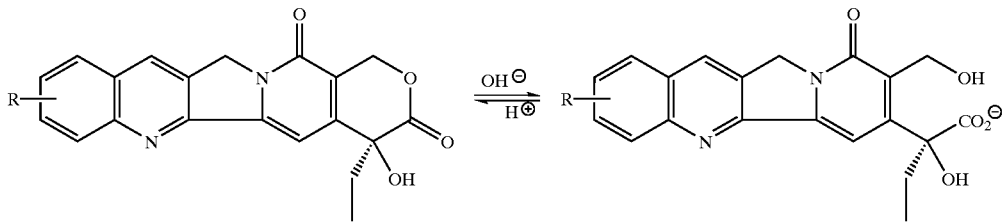

The hydrolysis reaction of the biological active lactone ring of camptothecins with water at higher pH gives the biologically inactive open form. Additionally, the hydrolysis problem with CPT and its analogs is exacerbated in human blood because the predominant blood serum albumin preferentially binds to the carboxylate form, which shifts the lactone/carboxylate equilibrium toward the inactive form (J. Biochem., 212, 285–287, 1993; Biochemistry, 33, 10325–10336, 1994; Biochemistry, 33, 12540–12545, 1994). Accordingly, preserving the lactone ring of the molecule for a sufficient time for the tumor cells to cycle through the S-phase is a major challenge and has been the focus of a considerable amount of research.

A number of attempts have been made to provide derivatives of camptothecin having greater biological activity and enhanced stability. Many of these compounds are the products of modifications on the A, B, and C rings of the molecule, but few of these modifications have enhanced the stability of the lactone ring under physiological conditions. Other approaches have been more successful. For instance, acylation of 20-OH group provides a useful tool for the protection of lactone ring E. Wall et al., U.S. Pat. No. 4,943,579, describes several acylated camptothecin compounds having water solubility, although the lactone may not remain intact under physiological conditions. U.S. Pat. No. 5,968,943 to Cao et al. discloses CPT-derivatives which are effective antitumor agents. Unfortunately, because mammalian physiological conditions break down all known CPT-derivatives, a need still exists for new CPT-derivatives and associated delivering systems for medical purposes.

In particular, there is a continuing need to modify 20(S)-camptothecin to enable the lactone ring to remain intact at normal physiological conditions, while retaining the structural elements, i.e. 20-hydroxyl and lactone ring E, for its antitumor activity. Accordingly, the present invention describes new CPT-derivatives which delay the opening of the lactone ring E, enhancing and prolonging the antitumor activity as compared to the mother analog, CPT. Thus, the present invention overcomes one or more of the above-described disadvantages.

SUMMARY OF THE INVENTION

Accordingly, it is an object of the present invention to provide cascade esters of camptothecins which remain intact longer in a mammalian body, particularly in a human body.

It is another object of the present invention to provide new CPT-derivatives which retain the lactone ring E and the 20-hydroxyl group intact, which are important for antitumor or anticancer activity.

It is still another object of the present invention to use these compounds in a liposomal delivery system for living mammals.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention relates to a compound of the general formula:

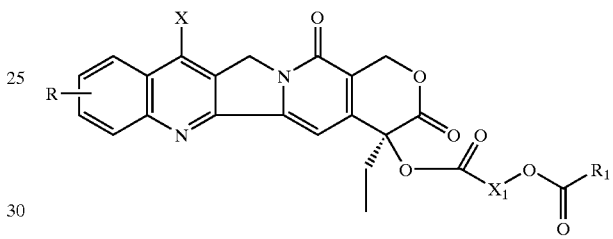

In this formula, the R group represents one or more substituents on one of the rings of the structure above. In particular, R represents H, $NO_2$, $NH_2$, $N_3$, —OH, a halogen (e.g., F, Cl, Br, I), carboxyl (COOH), a $C_{1-16}$ alkyl group, $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_n NR_2^7$ (where $R^7$ is H, or a $C_{1-8}$ alkyl group, n is an integer of from 1 to about 8), hydroxyl, SH, $SR^8$ (where $R^8$ is a $C_{1-8}$ alkyl group, or an unsubstituted or substituted phenyl group), a carbonyl group, (e.g., $COR^9$, where $R^9$ can be a $C_{1-8}$ alkyl group, an unsubstituted phenyl group, or a substituted phenyl group), a $SiR_3^{10}$ (where $R^{10}$ can be a $C_{1-4}$ alkyl group). The R group is respectively positioned at the 9, 10, 11, or 12 position of ring A. R can also be a disubstituted 10, 11—O—$(CH_2)$—O-group (where y can be an integer of from 1 to 3). R can also be $C_{2-12}$ alkenyl group(s), $CF_3(s)$, $CCl_3$ (s), $CH_2$ F(s), $CH_2$ Cl(s), $CHF_2(s)$, $CHCl_2(s)$, $OR^{12}(s)$ (where $R^{12}$ can be a $C_{1-8}$ alkyl group, or a $C_{2-8}$ alkenyl group, or an aromatic group), $NR_2^{13}(s)$ (where $R^{13}$ can be H, or $C_{1-4}$ alkyl group). X represents H, a $C_{1-8}$ alkyl group, a $C_{2-8}$ alkenyl group, a $C_{1-8}$ alkoxyl group, an aroxyl group, a $SiR_3^{11}$ group (where $R^{11}$ can be a $C_{1-4}$ alkyl group), or $CH_2NZY$ where Z and Y can be, independently, H, $C_{1-4}$ alkyl, or a $C_{1-4}$ halogenated alkyl group. Preferably, R can be hydrogen, halogen, halogen containing group, alkyl group (e.g. $C_1$–$C_{15}$ alkyl group), —$NO_2$, —OH, alkoxy, or —$NH_2$. $X_1$ can be an alkyl chain of the type (—$CH_2$—)$_n$ where n can be 1 through 15, or an aromatic radical, such as —$Ar(Y_1Y_2Y_3Y_4)$, where Ar can be an aromatic radical (e.g., acyl,benzyl), $Y_1$, $Y_2$, $Y_3$, and $Y_4$, which can be the same or different, can be hydrogen, alkyl groups, halogen groups, nitro groups, cyano groups, amino groups, hydroxyl groups, carbonyl groups, or carboxyl groups, and $R_1$ can be an alkyl group, a halo alkyl group, or an aromatic group.

The present invention also relates to a method for treating cancer and/or malignant tumors in a mammal and comprises administering an effective amount of one or more of the above CPT-derivatives, which may include any delivery system or other therapeutic means.

Also, the present invention relates to methods of making the compounds of the present invention to provide haloalkyl esters of camptothecins which remain intact longer in a mammalian body, particularly in a human body.

It is to be understood that both the foregoing general description and the following detailed description are exemplary and explanatory only and are intended to provide further explanation of the present invention as claimed.

DETAILED DESCRIPTION OF THE INVENTION

In the most general sense, the present invention relates to cascade esters of camptothecins and their use for medicinal purposes. Camptothecins ("CPTs") have considerable anti-tumor and anti-cancer activity, but these compounds are susceptible to degradation under normal physiological conditions, and the metabolites produced often exhibit toxic properties. Therefore, the present invention provides CPT analogues which remain intact longer in a mammalian body, particularly in the human body, thus enhancing the anti-tumor and anti-cancer effects without producing undesirable side effects. In another embodiment, the present invention provides new CPT-derivatives which retain the lactone ring E and the 20-hydroxyl group intact, as prior research has shown that these structural features are important for anti-tumor or anticancer activity. The compounds of the present invention are bio-active and/or are a pro-drug that generates a bio-active compound.

Metabolism studies of camptothecin in human plasma carried out in the laboratory showed that the only metabolite detected is the ring-opened sodium carboxylate salt which is toxic and inactive. The measurement of pharmacokinetics for CPT in human plasma indicates that the half-life time of the drug with lactone intact is 30 min. These results imply that the drug will lose 90% of its activity and produce many toxicities or side effects in a very short time after a patient takes it.

Comparative pharmacological studies in mice and humans have demonstrated that in mice the majority of the CPT present in the plasma after intrastomach administration is of the closed lactone form, approximately 54% of the area under the curve. In humans, on the contrary, only about 0.4% of the area under the curve after oral administration of CPT is in the form of closed lactone ring.

This difference between a mouse and a human is caused by the fact that although the blood pH of the mouse and human are the same, i.e., 7.4, the human albumin, which catalyzes the conversion of CPT into its sodium salt is ~100 times more efficient in this process than mouse albumin (Mi and Burke, Biochem. 33:12540, 1994).

In view of the different success rates in using CPT analogs as anticancer or antitumor agents in mice and humans, as discussed previously, it is clear that delaying the opening of the lactone ring under biological conditions is essential to enhance the beneficial properties of CPTs, as well as avoiding the negative side effects of metabolites. Therefore, to achieve these goals, the present invention provides C-20 hydroxyl of CPT to form new CPT analogs with desirable biological properties. Preferably, the present invention relates to "cascade" esters, of the general structure given below.

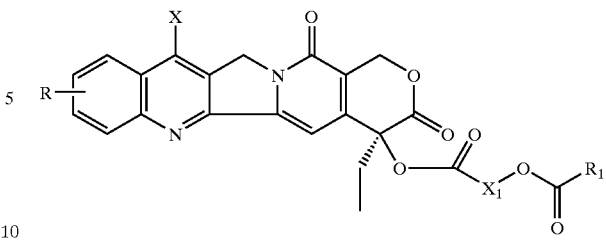

In this formula, the R group represents substituents on one of the rings of the structure above. In particular, R represents H, $NO_2$, $NH_2$, $N_3$, —OH, a halogen (e.g., F, Cl, Br, I), carboxyl (COOH), a $C_{1-16}$ alkyl group, $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_n NR_2^7$ (where $R^7$ can be H, or a $C_{1-8}$ alkyl group, n can be an integer of from 1 to about 8), hydroxyl, SH, $SR^8$ (where $R^8$ can be a $C_{1-8}$ alkyl group, an unsubstituted phenyl group, or a substituted phenyl group), a carbonyl group, (e.g., $COR^9$, where $R^9$ can be a $C_{1-8}$ alkyl group, an unsubstituted phenyl group, or a substituted phenyl group), a $SiR_3^{10}$ (where $R^{10}$ can be a $C_{1-4}$ alkyl group). The R group can be respectively positioned at the 9, or 10, or 11, or 12 position of ring A. R can also be a disubstituted 10, 11—O—$(CH_2)_y$—O-group (where y can be an integer of from 1 to 3). R can also be $C_{2-12}$ alkenyl group(s), $CF_3$(s), $CCl_3$(s), $CH_2F$(s), $CH_2Cl$(s), $CHF_2$(s), $CHCl_2$(s), OH(s), $OR^{12}$(s) (where $R^{12}$ can be a $C_{1-8}$ alkyl group, or a $C_{2-8}$ alkenyl group, or an aromatic group), $NR_2^{13}$(s) (where $R^{13}$ can be H, or $C_{1-4}$ alkyl group). X represents H, a $C_{1-8}$ alkyl group, a $C_{2-8}$ alkenyl group, a $C_{1-8}$ alkoxyl group, an aroxyl group, a $SiR_3^{11}$ group (where $R^{11}$ can be a $C_{1-4}$ alkyl group), or $CH_2NZY$ where Z and Y can be, independently, H, $C_{1-4}$ alkyl, or a $C_{1-4}$ halogenated alkyl group. Preferably R can be a hydrogen, halogen, halogen containing group, an alkyl group (e.g., $C_1-C_{15}$ alkyl group), —$NO_2$, —OH, alkoxy, or —$NH_2$. $X_1$ can be an alkylene group, such as an alkyl chain of the type (—$CH_2$—)$_n$ where n can be 1 through 15, or an aromatic radical, for example, of the type —Ar($Y_1Y_2Y_3Y_4$), where $Y_1$, $Y_2$, $Y_3$, and $Y_4$, which can be the same or different, can be hydrogen, alkyl groups, halogen groups, nitro groups, cyano groups, amino groups, hydroxyl groups, carbonyl groups, or carboxyl groups, Ar can be an aromatic radical, such as aryl and benzyl. $R_1$ can be an alkyl group, a halo alkyl group, an aromatic group, or a group including various different functional group as shown below in example 2 (i.e., ester of acetylsalicylic acid, or derivatives thereof).

Some specific examples of alkyl groups that can be used are —$CH_3$, —$CH_2CH_3$, $CH_3$ $CH_2CH_2$—, $CH_3(CH_2)_3$—, $CH_3(CH_2)_4$—, $CH_3(CH_2)_5$—, and $CH_3(CH_2)_{6-17}$—, $(CH_3)_2CH$—, $CH_3$—$CH_3$—$CH_2CH$—$CH_3$, $(CH_3CH_2)_2CH$—, $(CH_3CH_2CH_2)_2CH$—, $(CH_3)_3C$—, $CH_3(CH_3CH_2)_2C$—.

Some specific examples of alkylenyl alkenyl groups that can be used are $CH_2$=CH—, $CH_3CH$=CH—, $CH_3CH$=C($CH_3$)—, $CH_3CH$=$CHCH_2$—, $CH_3CH_2CH$=$CHCH_2$—, $CH_3(CH_2)_{3-15}$ CH=CH—, $CH_3CH$=CH—$(CH_2)_{3-15}CH_2$, $CH_2$=CH—CH=CH—, $CH_3CH$=CH—CH=CH—, $CH_3(CH_2)_{3-6}$—CH=CH—CH=CH—$(CH_2)_{3-6}$—$CH_2$—.

Some specific examples of cycloalkoxyl groups that can be used are

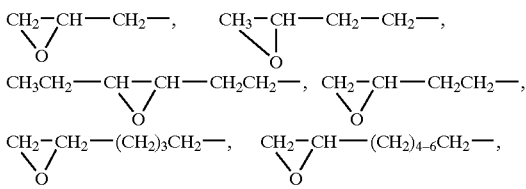

Some specific examples of alkoxyl groups that can be used are MeO—, EtO—, n—$C_3H_7$—, i—$C_3H_7$—O—, n—$C_4H_9$—O—, i—$C_4H_9$—O—, t—$C_4H_4$—O—, n—$C_5H_{11}$O—, $(CH_3)_2CHCH_2CH_2O$—,

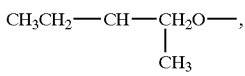

$(CH_3C_2)_2CH$—O—, n—$CH_6H_{13}$—O—, n—$C_7H_{15}$—O—, n—$C_8H_{17}$—O—.

Some specific examples of aroxyl groups that can be used are p—$CH_3OC_6H_4$—, m—$CH_3O$—$C_6H_4$—, o—$CH_3OC_6H_4$—, o,p-Dimethoxyl phenyl-, m,m-Dimethoxyl phenyl-, m,p-Dimethoxyl phenyl-, o—$CH_3CH_2OC_6H_4$—, m—$CH_3CH_2OC_6H_4$—, p—$CH_3CH_2O$—$C_6H_4$—.

Some specific examples of cycloalkyl groups that can be used are cyclo-$C_3$, cyclo-$C_4$, cyclo-$C_5$, cyclo-$C_6$, cyclo-$C_7$, cyclo-$C_8$, alkyl substituted cyclo-$C_3$, alkyl substituted cyclo-$C_4$, alkyl substituted cyclo-$C_5$, alkyl substituted cyclo-$C_6$, alkyl substituted cyclo-$C_7$, and alkyl substituted cyclo-$C_8$ (where alkyl includes preferably those alkyl groups described above).

Some examples of substituted and unsubstituted phenyl groups that can be used are $C_6H_5$—, (o,m,p) $CH_3C_6H_4$—, halogen substituted phenyl groups ($XC_6H_4$, wherein X=F, Cl, Br, I), (o,p,m) $CH_3OC_6H_4$—, (o,m,p) $NO_2C_6H_4$—, (o,m,p)$NH_2C_6H_4$—, (o,m,p) $CNC_6H_4$—.

Some examples of carbonyl groups that can be used are

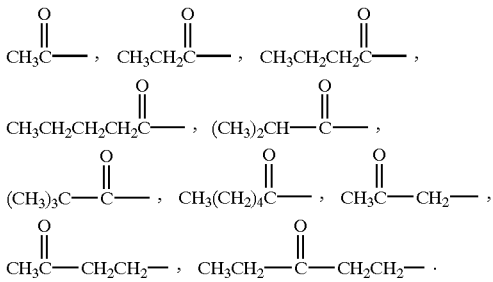

As noted above, delaying the opening of the lactone ring is a central goal in improving the biological efficacy of the camptothecin series of compounds. In keeping with this observation, the present invention provides new strategies of functionalizing the C-20 hydroxyl group with a protective group would be a productive way of enhancing the biological properties of the camptothecin series, as it appears that cleavage of the protective group precedes the opening of the lactone ring. One might contemplate various strategies designed to slow the rate of cleavage of the protecting group from the C-20 hydroxyl. One might even consider functionalizing the C-20 hydroxyl group with a permanent protecting group. However, it appears that the parent compound, CPT, is the active agent from the biological standpoint. Therefore, one cannot merely protect the C-20 hydroxyl group with a permanent protecting group, since liberation of the parent compound is ultimately necessary to maximize its therapeutic potential. In other words, one must slow, but not completely stop, the rate of cleavage of the protective group. Further, the compounds described above are preferably active in their form set forth above.

If a single protective group improves the biological properties of camptothecin analogs, one might assume that protecting the C-20 hydroxyl with two protecting groups would be even more desirable. Obviously, it is not possible to add a discrete second protective group after a first protecting group has cleaved away under biological conditions, but it is possible to make the cleavage of the protective group involve a multi-step process, thus creating the functional equivalent of two protective groups. More specifically, one could envision a protective group that would cleave in more than one position before liberating the parent compound, CPT. Such multiple cleavages of organic groups, generally esters or ester-like compounds, are known as "cascade" chains, in that one step or transformation naturally leads to another, just as water flowing down as a series of waterfalls always follows a certain sequence.

With this in mind, the present invention provides CPT derivatives having a novel protective group that cleaves in two different positions in a cascade sequence before generating the parent compound. It is believed that the first cleavage occurs at the outside ester bond when the drug circulates in the blood, and the second cleavage occurs in the tumor tissues to liberate the active parent compound. Therefore, the sequential cleavage of the esters allows targeting of the tumor or cancer, in that generation of the parent compound occurs at the site of the tumor or cancer that is most susceptible to inhibition by the CPT.

The preferred sequence of events is shown below.

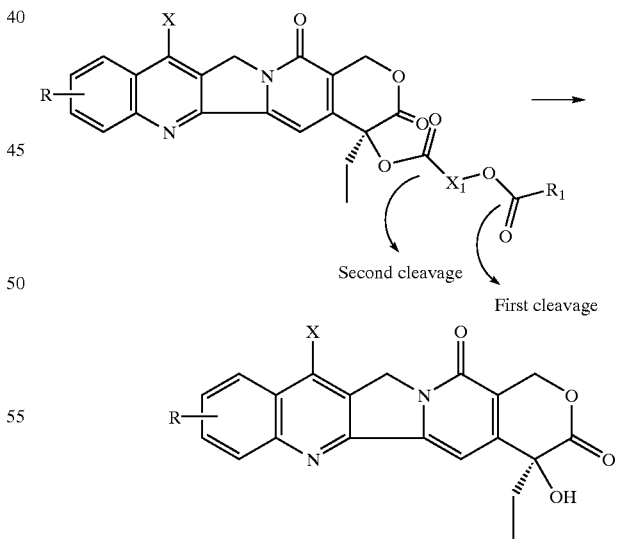

The compounds of the present invention may be produced by more than one synthetic pathway, and variations of the substituents on the protective groups are possible, as is clear to persons skilled in synthetic organic chemistry. A representative example of producing a cascade ester of camptothecins is set forth and discussed directly below.

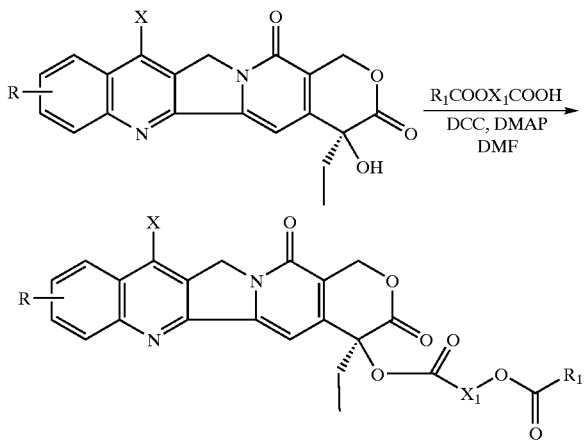

The general method involves reacting the CPT with an appropriately substituted organic acid in the presence of a suitable solvent, such as dimethyl formamide (DMF), and compounds known to facilitate esterifications. An example of a compound known to facilitate esterification is a coupling agent like an dialkylcarbodiimide, an example of which is dicyclohexylcarbodiimide (DCC) and dimethylaminopyridine (DMAP), an example of which is 4-dimethylaminopyridine (or other suitable catalyst). Preferably the reaction takes place at room temperature ($\approx 25°$ C.) and under nitrogen atmosphere, wherein the reaction time is from about 1 day to about 1 week.

The purity and the concentration of the CPT are not important. The solvent can be any solvent that does not include a hydroxy group, which can react with acylating and/or esterification agents. Thus, any solvent can be used that is capable of dissolving the CPT, but does not react with the acylating/esterification agent. An example of suitable solvent is chloroform, and more preferably, DMF.

The solvents used in this reaction are commonly available and do not need to be pure (e.g. it can be industrial-grade solvent); however, for organic reactants, it is preferable to use highly purified solvents. Additionally, the solvents can have any pH that does not cause the CPT to decompose. Preferably, the solvents are not basic, and more preferably, the solvents are neutral.

The pH of the organic acid in the present invention is not important. Preferably, the organic acid acts as the acylating agent. More preferably, the organic acid is acetylsalicylic acid. Generally, the organic acid can have a general formula $R_1COOX_1COOH$, wherein $X_1$ can be an alkylene group, such as an alkyl chain of the type $-CH_{2-n}$ where n can be 1 through 15, or an aromatic radical, for example, of the type $-Ar(Y_1Y_2Y_3Y_4)$, where $Y_1$, $Y_2$, $Y_3$, and $Y_4$, which can be the same or different, can be hydrogen, alkyl groups, halogen groups, nitro groups, cyano groups, amino groups, hydroxyl groups, carbonyl groups, or carboxyl groups, Ar can be an aromatic radical, such as aryl and benzyl. $R_1$ can be an alkyl group, a halo alkyl group, an aromatic group, or a group consisting of various different functional groups as shown below in example 2 (i.e., ester of acetylsalicylic acid, or derivatives thereof). The organic acids of the present invention are commercially from places such as Aldrich Chemical Co., Milwaukee, Wis. One example of an organic acid that can be used is acetylsalicylic acid, which is commercially available. The organic acids of the present invention can also be synthesized to have the desired chemistry.

In the present invention, any catalyst can be used that facilitates esterifiication. One example of a commonly used catalyst in this type of reaction is DMAP; however, other catalysts can also be used that have the same characteristics as the DMAP. The purity of the catalyst is not important, so long as the impurities do not react with the reactants.

A coupling agent can also be used. One example of a commonly used coupling agent is DCC. If DCC is used in the present invention, then it is preferable to use a catalyst, such as DMAP or other catalysts having the same characteristics as DMAP.

As a representative example of making the desired product, the CPT can be added to a solvent, which preferably is DMF. The ratio of the solvent to the CPT can be from about 10 ml or less of solvent to about 1 gram of the CPT to about 1000 ml of the solvent to about 1 gram of CPT. However, at a ratio 1000 ml of the solvent to 1 gram of CPT more reaction time may be required.

The coupling agent, such as DCC, can also be added to the solvent (DMF) before, during, or after adding the CPT to the solvent. Preferably, the molar ratio of the DCC to the CPT is about 1 to about 2.2.

Similar to the DCC, which can be added to the solvent at any time, the catalyst can also be added to the solvent (DMF) before, during, or after adding the CPT or the DCC to the solvent. The amount of the catalyst added to the solvent for the reaction to properly take place can be half or less than half of the molar amount of the DCC added to the solvent.

Additionally, an organic acid, which can act as the acylating agent having a general formula $R^1COOX_1COOH$, can also be added to the above mixture. The organic acid, which is preferably acetylsalicylic acid or the acid employed in example 2, shown below, can be added to the solvent before, during, or after adding the CPT, the DCC, and the catalyst to the solvent. The organic acid, such as acetylsalicylic acid, can be added in any amount; however, it is preferable to not add the organic acid (acetylsalicylic acid) in large excess. More preferably, the molar ratio of the organic acid to the DCC is about 1:1.

Preferably, all of the above compositions are added to a reactor and are agitated under an inert atmosphere, such as $N_2$, at room temperature, and at ambient pressure. It is preferable to agitate the solution at a sufficient agitation speed to form the desired product. Preferably, the agitation speed is moderate, which is about 100 rpm to about 250 rpm.

The reaction time depends on several variables, such as the ratio of the solvent to the CPT. The reaction is preferably continued until the reaction is completed, which can be determined for instance, by a color change in the solution. Additionally, when the solution turns from a homogeneous solution into a suspension solution, the reaction is completed. The reaction may take from about 1 day to about 1 week to complete.

After the completion of the reaction, the solvent can be removed by any commonly known separation methods, such as an evaporation method or a vacuum system method. The residue that remains after removing the solvent can be filtered by a column chromatography. The residue can be chromatographically separated on silica, using THF-methylene chloride as the eluting solvent. The final product, identified as CZ183, was obtained as a yellow powder in a 38% yield after the solvents were removed by a rotary evaporator.

The yields of the final products in the synthetic pathways set forth above typically are 10–90%, depending on the exact reaction conditions, the purity of the starting materials, the nature of the acylating agent, the choice of solvent, and other factors or parameters common to synthetic organic chemistry. The methods of producing the compounds of the present invention, as set forth above, are not meant to be exclusive or limiting, but rather are exemplary only, and other means for generating these compounds or optimizing the reaction conditions are possible for persons skilled in the art.

The compounds of the present invention are effective in treating malignant tumors or cancers in mammals. As used herein, the term "malignant tumor" is intended to encompass all forms of human carcinomas, sarcomas and melanomas which occur in the poorly differentiated, moderately differentiated, and well differentiated forms.

More specifically, the compounds of the present invention and formulations of the present invention can be used in the treatment of a number of tumors and/or cancers including, but not limited to, human cancers of the lung, breast, colon, prostate, melanoma, pancreas, stomach, liver, brain, kidney, uterus, cervix, ovaries, urinary track, gastrointestinal, and other solid tumors which grow in an anatomical site other than the blood stream, as well as blood borne tumors such as leukemia. Other solid tumors include, but are not limited to, colon and rectal cancer. The compounds of the present invention are also useful as inhibitors of the enzyme topoisomerase I.

The compounds of the present invention can be administered by any acceptable route including, but not limited to, orally, intramuscularly, transdermally, intravenously, through an inhaler or other air borne delivery systems, and the like. Preferably, the compounds and the formulations of the present invention are administered orally, intramuscularly, or transdermally and most preferably delivered orally. Examples of transdermally delivery systems can be found, for instance in U.S. Pat. Nos. 5,552,154 and 5,652,244 incorporated in their entirety by reference herein. The compounds or formulations of the present invention can also be administered to a patient through a liposome system such as ones described in U.S. Pat. Nos. 5,882,679; 5,834,012; 5,783,211; 5,718,914; 5,631,237; 5,552,156; 5,059,421; 5,000,958; 5,874,105; 5,567,434; 5,549,910; 5,043,165; 5,736,156; 5,567,433; and 4,663,161, all incorporated in their entirety by reference herein. The compounds of the present invention may be incorporated or encapsulated in, surrounded or entrapped by, or otherwise restrained by a liposomal delivery system to form "liposomal prodrugs" using the compounds of the present invention. Other commonly used methods include, for example, gelatin capsules for oral administration, as well as formulations such as microsuspensions of the liposomal prodrugs in lipid and in lipid-like emulsions (e.g. -Intralipid 20, cottonseed oil and peanut oil) for intramuscular administration and inclusion in cholesterol pellets for subcutaneous long-term administration.

When taken orally by patients, the prodrugs are rapidly introduced into the bloodstream of a patient and readily converted to the parent compound in the body. Conversion of the prodrugs to the mother compound, CPT, is mediated by a group of enzymes called esterases present in the blood of many animals, including humans. Since the prodrugs are rapidly distributed throughout the body in a short period of time after delivery, these compounds exist at a very low concentration at the time they undergo enzymatic hydrolysis to the parent compound, and this prevents the CPT from precipitating in the bloodstream.

Another method of administering the compositions of the present invention is by a transdermal or transcutaneous route. One example of such an embodiment is the use of a patch. In particular, a patch can be prepared with a fine suspension of a prodrug of the present application in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well for delivering the prodrugs. The patch can contain the CPT-derivative-containing prodrug of the present invention in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

In addition, the compounds and formulations of the present invention can be used in combination with other drugs and formulations for the treatment of cancers such as taxol, taxotere, or their derivatives, as well as cisplatin and derivatives thereof.

As used herein, an "effective amount" of the compounds and formulations of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on $mg/M^2$ of body surface) is described by E. J. Freireich et al., *Cancer Chemother. Rep.*, 50(4):219 (1966). Body surface area may be approximately determined from the height and weight of an individual (see, e.g., *Scientific Tables*, Geigy Pharmaceuticals, Ardsley, N.Y. pp. 537–538 (1970). A preferred effective amount of the camptothecin compounds in the present invention can range from about 12.5 to about 31.3 $mg/m^2$ of body surface per day, and for the prodrugs an effective amount can range from about 12.5 to about 3000 $mg/M^2$ of body surface area per day based on the weight of the prodrug and the delivery system.

The preferred effective amounts or dosages of the prodrugs of the present invention in mice are from about 1 to about 400 mg prodrug per kg of body weight twice a week for an intramuscular route and from about 0.75 to about 150 mg prodrug/kg/day for the oral route. Effective amounts or dosages of the prodrugs of the present invention in mice are, for instance, from about 1.5 mg/kg/week to about 1000 mg/kg/week of the prodrug for the transdermal route. For all of the administering routes, the exact timing of administration of the dosages can be varied to achieve optimal results. Generally, when using Intralipid 20 as the liposomal carrier for the CPT-derivative, the actual dosage of CPT-derivative reaching the patient will be less. This is due to some loss of the CPT-derivative on the walls of the syringes, needles and preparation vessels, which is prevalent with the Intralipid 20 suspension. Generally, from about 1 mg to about 4 mg of CPT-derivative is added to about 0.1 ml to about 1 ml of lipid carrier.

The compounds used in the present invention may first be combined with pharmaceutically acceptable carriers or diluents, such as Intralipid 10 or 20 or natural oils, or other suitable emulsifiers for lipophilic compounds, prior to being incorporated, encapsulated, surrounded, entrapped, or otherwise restrained in, on, or by the lipsomal delivery system.

Liposomes have been used successfully to administer medications to cancer patients, and have been shown to be useful clinically in the delivery of anticancer drugs such as doxorubicin, daunorubicin, and cisplatinum complexes. Forssen, et al., Cancer Res. 1992,52: 3255–3261; Perez-Soler, et al. Cancer Res. 1990, 50: 4260–4266; and, Khokhar, et al. J. Med. Chem. 1991, 34: 325–329, all of which are incorporated herein in their entireties by reference.

Administration involving liposomes may include, for example, lipids such as cholesterol, phospholipids, or micelles comprised of surfactant such as, for example, sodium dodecylsulfate, octylphenolpolyoxyethylene glycol, or sorbitan mono-oleate. Typically, the prodrugs bind to the lipid bilayer membrane of the liposome with high affinity. The liposome bound prodrug can preferably intercalate between the acyl chains of the lipid. The lactone ring of the camptothecin-derivative, membrane-bound prodrug is thereby removed from the aqueous environment inside and outside of the liposome and thus protected from hydrolysis. Since the liposome-bound drug is protected from hydrolysis, the antitumor activity of the drug is preserved. For the camptothecin prodrugs which have a lower affinity for the liposome membrane and thus disassociate from the liposome membrane to reside in the interior of liposome, the pH of the interior of the liposomes may be reduced thereby preventing hydrolysis of such camptothecin-derivative prodrugs.

Similarly, micelles have also been used to deliver medications to patients, (Brodin et al., Acta Pharm. Suec. 19 267–284 (1982)) and micelles have been used as drug carriers and for targeted drug delivery, (D. D. Lasic, Nature 335: 279–280 (1992); and, Supersaxo et al., Pharm. Res. 8: 1286–1291 (1991)), including cancer medications, (Fung et al., Biomater. Artif. Cells. Artif. Organs 16:439 et. seq. (1988); and Yokoyama et al., Cancer Res. 51: 3229–3236 (1991)), all of which are incorporated herein in their entireties by reference.

The liposomes and/or micelles of the present invention containing the camptothecin-derivative prodrugs can be administered to a cancer patient. The liposomes and/or micelles are carried by the circulatory system to the cancer cells where the membrane of the vesicle fuses to the membrane of the cancer cell thereby releasing the camptothecin-derivative prodrug to the cancer cell, or where the liposomes and/or micelles remain adjacent to the cancer cells, the camptothecin-derivative prodrug diffuses from the liposomes and/or micelles to be taken up by the cancer cells.

Any lipid or mixture of lipids which forms liposomes and/or micelles is suitable for use in the present invention. The liposomes and/or micelles may be coated with polyethyleneglycol or $GM_1$ protein which assists the particles in avoiding the reticuloendothelial system.

In addition, micelles may be composed of lipid, such as phospholipid, and mixtures of lipids. Also, micelles may be composed of both lipid and a suitable surfactant.

The preparations of many liposomes and micelles are described in U.S. Pat. Nos. 5,552,156, and 5,736,156, which are herein incorporated in their entireties by reference. A preferred group of liposomal delivery systems which may be used in accordance with the present invention include those described in U.S. Pat. Nos. 5,552,156 and 5,736,156, which are herein incorporated in their entireties by reference. Other liposomal delivery systems which may be employed in accordance with the present invention include liposomes containing active agents aggregated with lipids or surfactants as described in U.S. Pat. Nos. 5,827,533 and 5,882,679; lipid vesicles formed with alkyl ammonium fatty acid salts as described in U.S. Pat. No. 5,874,105; liposomes for encapsulating active agent dry powder compositions as described in U.S. Pat. No. 5,783,211; liposomal drug delivery systems for topical patches as described in U.S. Pat. No. 5,718,914; the liposomes described in U.S. Pat. No. 5,631,237; the liposome and lipid complex compositions described in U.S. Pat. Nos. 5,549,910 and 5,077,057; the liposomes used for sustained release of steriodial drugs as described in U.S. Pat. No. 5,043,165; the liposomes described in U.S. Pat. No. 5,013,556; and the liposomes described in U.S. Pat. No. 4,663,161; all of which are herein incorporated in their entireties by reference.

The present invention also inhibits topoisomerase I in mammals be administering an effective amount of one of the above-identified compounds using, for instance, the amounts described above. Finally, one of the most important advantages provided by the present invention relates to the relatively low or no apparent overall toxicity of the compounds administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity. In this respect, the low toxicity of the compounds and formulations of the present invention represent a significant advance over the prior art.

The present invention will be further clarified by the following examples, which are intended to be purely exemplary of the present invention.

EXAMPLES

All glassware referenced in the examples was baked at 80–100° C. for a minimum of 2 hours before being used. Melting points were obtained with a MEL-TEMP melting point apparatus and were uncorrected. The $^1$H and $^{13}$C NMR spectra were obtained at 270.05 MHZ with a JEOL GX-270 WB NMR spectrometer. Chemical shifts are reported in parts per million (δ scale), employing tetramethylsilane as an internal standard. In reporting the NMR data, the following abbreviations are used: coupling constants in Hertz (J), singlet (s), doublet (d), triplet (t), broad singlet (brs), multiplet (m), etc. Mass Spectra were recorded using a VG ZAB-SEQ mass spectrometer (VG Analytical Co., England) with a resolution of 10000. The numbering system used for the carbon backbone of camptothecin is shown in formula (X).

Example 1

Preparation of CZ183:

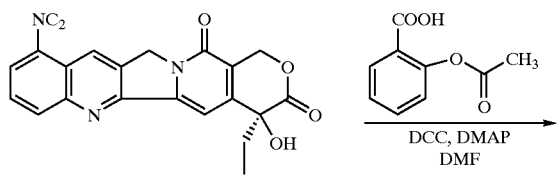

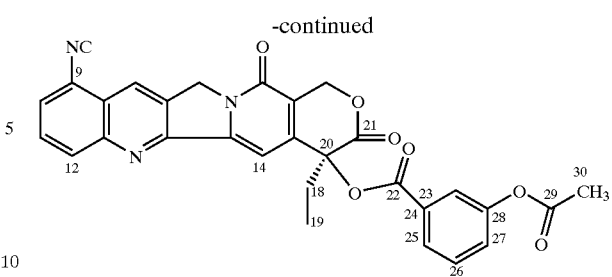

1.5 grams (0.0038 mol) of a CPT derivative, 9-nitrocamptothecin, is dissolved in approximately 100 ml of DMF. To this solution is added 1.70 grams (0.0083 mol) of DCC and 0.41 grams (0.0034 mol) of DMAP, and 1.50 grams (0.0083 mol) of Acetylsalicylic acid in a three neck round bottom flask with mechanical stirring under an inert atmosphere at room temperature. After 96 hours, the solvent was removed under rotary evaporation and the residue chromatographically separated on silica, using THF-methylene chloride in the ratio of 1:15 (v/v) as the eluting solvent. After evaporation of the proper fraction, the final product, known as CZ183, was obtained as a yellow powder in a 38% yield. The numbering of the side chain is depicted above.

Example 2

Preparation of CZ207:

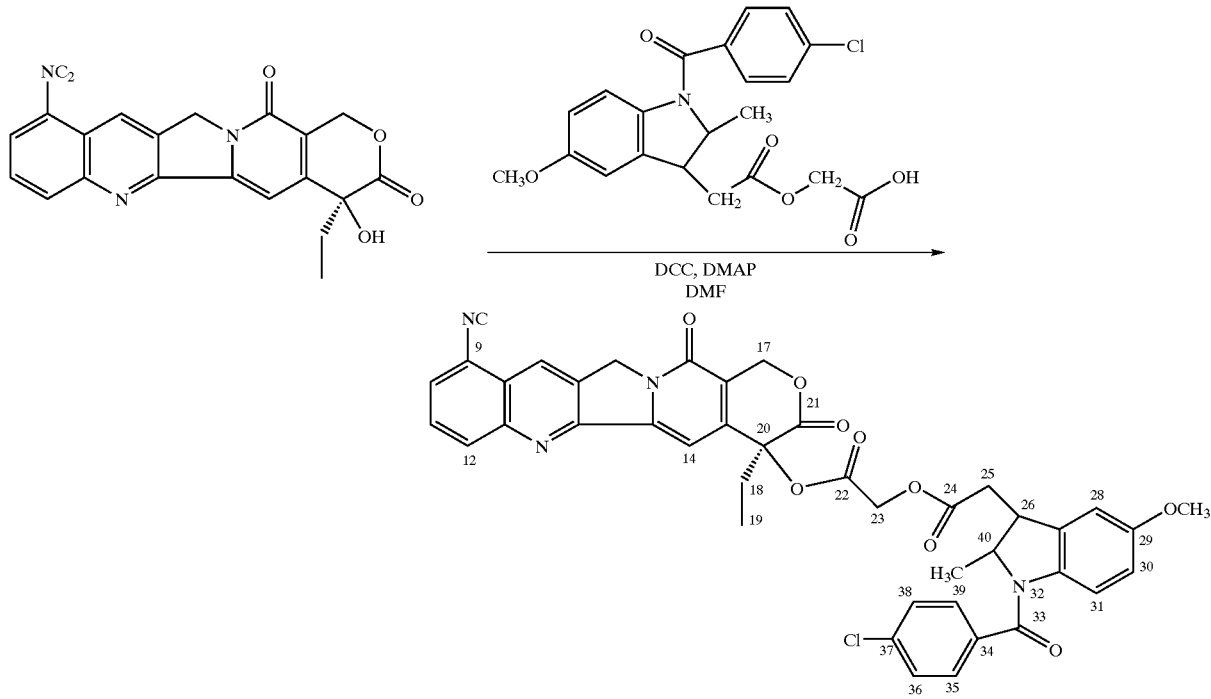

0.5 grams (0.0013 mol) of a CPT derivative, 9-nitrocamptothecin, is dissolved in approximately 60 ml of DMF. To this solution is added 0.75 grams (0.0036 mol) of DCC and 0.20 grams (0.0016 mol) of DMAP, and 1.0 grams (0.0024 mol) of 1-(4-chlorobenzyl)-5-methoxy-2-methyl-1H-indole-3-acetic acid carboxymethyl ester (or Acemetacin) [thus attaching Acemetacin-yl] in a three neck round bottom flask with mechanical stirring under a nitrogen atmosphere at room temperature. After 96 hours, the solvent was removed under vacuum and the residue chromatographically separated on silica, using THF-methylene chloride in the ratio of 1:10 (v/v) as the eluting solvent. The final product, known as CZ207, was obtained as a yellow powder in a 32% yield. The numbering of the side chain is depicted above.

$^1$H NMR (CDCl$_3$): 1.05(3H, t, J=7.08 HZ, C19 methyl protons), 2.200–2.36(2H, m, C18-methylene protons), 2.50 (3H, S, C40-CH$_3$), 3.95(3H, S, C29-methoxy protons), 4.10–4.50(2H, dd, J=17.20, 17.40 HZ, C25-methylene protons), 5.20–5.40(2H, dd, J=17.35, 17.52 HZ, C23-methylene protons), 5.65(2H, S, C5-methylene protons), 5.68–6.08(2H, dd, J=8.54, 8.58 HZ, C30-H, C31-H), 7.25 (1H, S, C14-H), 7.80(1H, S, C28-H), 8.0–8.20(4H, dd, J=8.65, 8.68 HZ, 35-H, C36-H, C38-H, C39-H), 8.35(1H, t, J=7.85 HZ, C11-H), 8.80–9.00(2H, dd=8.56, 8.62 HZ, C10-H, C12-H), 9.68(1H, S, C7-H). $^{13}$C: 7.9(C19, 13.2(C40-methyl carbon), 25.5, 29.5, 3.15(C18, C23, C25), 49.2(C29-methoxy carbon), 50.6(C5), 61.4(C17), 67.2(C20), 97.0 (C14), 100.8, 112.0, 112.1, 114.5, 121.0, 125.8, 127.0, 128.2, 129.1, 130.5, 131.0, 131.5, 133.6, 135.8, 136.5, 139.5, 145.0, 145.5, 145.6, 148.5, 154.5, 155.8, 156.9, 157.0(C2, C3, C6-C16a, C26-C40), 166.5, 167.5, 170.5 (C21, C22, C24).

Mass m/e(relative intensity): 790(m$^+$, weak), 415(40), 139(100), 111(20), 75(5); precise mass for C$_{41}$H$_{31}$N$_{14}$O$_{11}$Cl: Found 790.170, required 790.169.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims and equivalents thereof.

What is claimed is:

1. A compound of formula I:

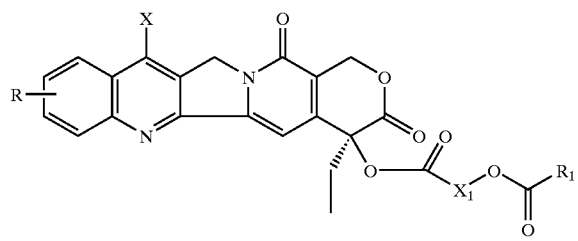

(I)

wherein R is H, NO$_2$, NH$_2$, N$_3$, a halogen, carboxyl, a C$_{1-16}$ alkyl group, a C$_{2-16}$ alkenyl group, a C$_{3-8}$ cycloalkyl group, a C$_{1-8}$ alkoxyl group, an aroxyl group, CN, SO$_3$ H, a C$_{1-8}$ halogenated alkyl group, (CH$_2$)$_n$NR$_2^7$, hydroxyl, SH, SR$^8$, a carbonyl group, a SiR$_3^{10}$; C$_{2-16}$ alkenyl group, CF$_3$, CCl$_3$, CH$_2$F, CH$_2$Cl, CHF$_2$, CHCl$_2$, OH, or OR$^{12}$ wherein the R group is respectively positioned at the 9, 10, 11, or 12 position of ring A; R$^{12}$ is a C$_{1-8}$ alkyl group, a C$_{2-8}$alkenyl group, or an aromatic group; R$^7$ is H or a C$_{1-8}$ alkyl group; n is an integer of 1 to 8; R$^8$ is a C$_{1-8}$ alkyl group or a phenyl group; R$^{10}$ is a C$_{1-4}$ alkyl group; X is H, a C$_{1-8}$ alkyl group, a C$_{2-8}$ alkenyl group, a C$_{1-8}$ alkoxyl group, an aroxyl group, a SiR$_3^{11}$ group, or CH$_2$ NZY; X$_1$ is an alkylene group or an aromatic radical, and R$_1$ is an alkyl group, a halo alkyl group, or an aromatic group wherein a carbon atom of X$_1$ and R$_1$ are attached to their respective carbonyl group thus each completing an ester linkage.

2. The compound of claim 1, wherein X$_1$ is —Ar (Y$_1$Y$_2$Y$_3$Y$_4$)—, wherein Ar is an aromatic radical and Y$_1$, Y$_2$, Y$_3$, and Y$_4$, which are the same or different, is hydrogen, an alkyl group, a halogen group, a nitro group, a cyano group, an amino group, a hydroxyl group, a carbonyl group, or a carboxyl group.

3. The compound of claim 2, wherein Y$_1$, Y$_2$, and Y$_3$, are each hydrogen, and Y$_4$ is an alkyl group, a halogen group, a nitro group, a cyano group, an amino group, a hydroxyl group, a carbonyl group, or a carboxyl group.

4. The compound of claim 2, wherein Y$_1$, and Y$_2$, are each hydrogen, and Y$_3$ and Y$_4$, which are the same or different, is an alkyl group, a halogen, a nitro group, a cyano group, an amino group, a hydroxyl group, a carbonyl group, or a carboxyl group.

5. The compound of claim 2, wherein Y$_1$ is hydrogen, and Y$_2$, Y$_3$, and Y$_4$, which are the same or different, is an alkyl group, a halogen group, a nitro group, a cyano group, an amino group, a hydroxyl group, a carbonyl group, or a carboxyl group.

6. The compound of claim 2, wherein Y$_1$, Y$_2$, Y$_3$, and Y$_4$, which are the same or different, is an alkyl group, a halogen group, a nitro group, a cyano group, an amino group, a hydroxyl group, a carbonyl group, or a carboxyl group.

7. A method for treating a tumor or cancer in a mammal comprising administering a composition comprising an effective amount of the compound of claim 1, wherein said tumor or cancer is responsive to said composition.

8. A method for treating a tumor or cancer in a mammal comprising administering a composition comprising an effective amount of the compound of claim 2, wherein said tumor or cancer is responsive to said composition.

9. A method for treating a tumor or cancer in a mammal comprising administering a composition comprising an effective amount of the compound of claim 3, wherein said tumor or cancer is responsive to said composition.

10. A method for treating a tumor or cancer in a mammal comprising administering a composition comprising an effective amount of the compound of claim 4, wherein said tumor or cancer is responsive to said composition.

11. A method for treating a tumor or cancer in a mammal comprising administering a composition comprising an effective amount of the compound of claim 5, wherein said tumor or cancer is responsive to said composition.

12. A method for treating a tumor or cancer in a mammal comprising administering a composition comprising an effective amount of the compound of claim 6, wherein said tumor or cancer is responsive to said composition.

13. The method of claim 7, wherein the tumor or cancer is present in the lung, breast, colon, prostate, pancreas, stomach, liver, brain, kidney, uterus, cervix, ovaries, urinary tract, rectal tract, or is a melanoma or leukemia.

14. The method of claim 8, wherein the tumor or cancer is present in the lung, breast, colon, prostate, pancreas, stomach, liver, brain, kidney, uterus, cervix, ovaries, urinary tract, rectal tract, or is a melanoma or leukemia.

15. The method of claim 9, wherein the tumor or cancer is present in the lung, breast, colon, prostate, pancreas, stomach, liver, brain, kidney, uterus, cervix, ovaries, urinary tract, rectal tract, or is a melanoma or leukemia.

16. The method of claim 10, wherein the tumor or cancer is present in the lung, breast, colon, prostate, pancreas, stomach, liver, brain, kidney, uterus, cervix, ovaries, urinary tract, rectal tract, or is a melanoma or leukemia.

17. The method of claim 11, wherein the tumor or cancer is present in the lung, breast, colon, prostate, pancreas, stomach, liver, brain, kidney, uterus, cervix, ovaries, urinary tract, rectal tract, or is a melanoma or leukemia.

18. The method of claim 12, wherein the tumor or cancer is present in the lung, breast, colon, prostate, pancreas, stomach, liver, brain, kidney, uterus, cervix, ovaries, urinary tract, rectal tract, or is a melanoma or leukemia.

19. A method for inhibiting the enzyme responsible for hydrolyzing the lactone ring of camptothecin under biological conditions, by administering a composition comprising the compound of claim 1 to a mammal.

20. A method for inhibiting the enzyme responsible for hydrolyzing the lactone ring of camptothecin under biological conditions, by administering a composition comprising the compound of claim 1 to a mammal, wherein the enzyme is topoisomerase I.

21. The compound of claim 1, wherein said alkylene group is —$CH_{2-n}$ where n is 1–15.

22. A method of making cascade esters of camptothecins of claim 1 comprising:

mixing camptothecins; a solvent; an organic acid; and a catalyst in any order.

23. The method of claim 22, further comprising mixing a coupling agent with said solvent.

24. The method of claim 23, wherein said coupling agent is dicyclohexylcarbodiimide.

25. The method of claim 23, wherein molar ratio of said coupling agent to camptothecins is about 1:2.2.

26. The method of claim 22, wherein said solvent is a solvent capable of dissolving said camptothecins, but incapable of reacting with said organic acid.

27. The method of claim 22, wherein said solvent does not include a hydroxy group.

28. The method of claim 22, wherein said solvent is a dimethyl formamide.

29. The method of claim 22, wherein said organic acid is mixed with said solvent before, during, or after contacting said camptothecins and said catalyst with said solvent.

30. The method of claim 22, wherein said organic acid is an acylating agent.

31. The method of claim 22, wherein said organic acid is an acetylsalicylic acid.

32. The method of claim 22, wherein said catalyst is dimethylaminopyridine.

33. The compound of claim 1, wherein $R_1$ is a methyl group, and $X_1$ is a $C_6H_4$ group.

34. The compound of claim 1, wherein $R_1$ is a 1-(4-chlorobenoyl)-5-methoxy-2-methyl-1H-indole-3-methyl group and $X_1$ is a methylene (—$CH_2$—) group.

* * * * *